United States Patent [19]

Takayama

[11] 4,367,024
[45] * Jan. 4, 1983

[54] PHOTOGRAPHING SYSTEM FOR ENDOSCOPE

[75] Inventor: Syuichi Takayama, Hachioji, Japan

[73] Assignee: Olympus Optical Co., Ltd., Tokyo, Japan

[*] Notice: The portion of the term of this patent subsequent to Sep. 29, 1998, has been disclaimed.

[21] Appl. No.: 193,648

[22] Filed: Oct. 3, 1980

[30] Foreign Application Priority Data

Oct. 13, 1979 [JP] Japan ............................. 54/132000

[51] Int. Cl.³ ............................................ G03B 29/00
[52] U.S. Cl. ...................................... 354/62; 354/132
[58] Field of Search ....................... 354/62, 132; 128/6

[56] References Cited

U.S. PATENT DOCUMENTS 3,599,630  8/1971  Sato et al. ............................... 354/62
4,086,583  10/1980  Takahashi .
4,291,961  9/1981  Takayama ............................. 354/62

FOREIGN PATENT DOCUMENTS 519611  10/1980  Japan .
52127429  10/1980  Japan .

Primary Examiner—Russell E. Adams
Attorney, Agent, or Firm—Frishauf, Holtz, Goodman & Woodward

[57] ABSTRACT

A photographing system for an endoscope comprises an endoscope including a light guide and an image guide, a camera unit including a shutter button for producing an instruction signal for starting a photographing cycle and a mirror shutter for opening a light path of an image supplied from an image guide; and a light source unit including a photographing light source for producing photographing light, an observation light source for producing observation light and a reflective mirror for switching light supplied to the light guide from the observation light to the photographing light. The camera unit further includes a switch for producing a light path switching signal for operating the reflective mirror simultaneously with the depression of the shutter button and a switch closed by the mirror shutter released a predetermined period of time after the depression of the shutter button and producing a signal for energizing the photographing light source. Thus, in the light source unit the photographing light source is turned on after the reflective mirror is switched.

5 Claims, 15 Drawing Figures

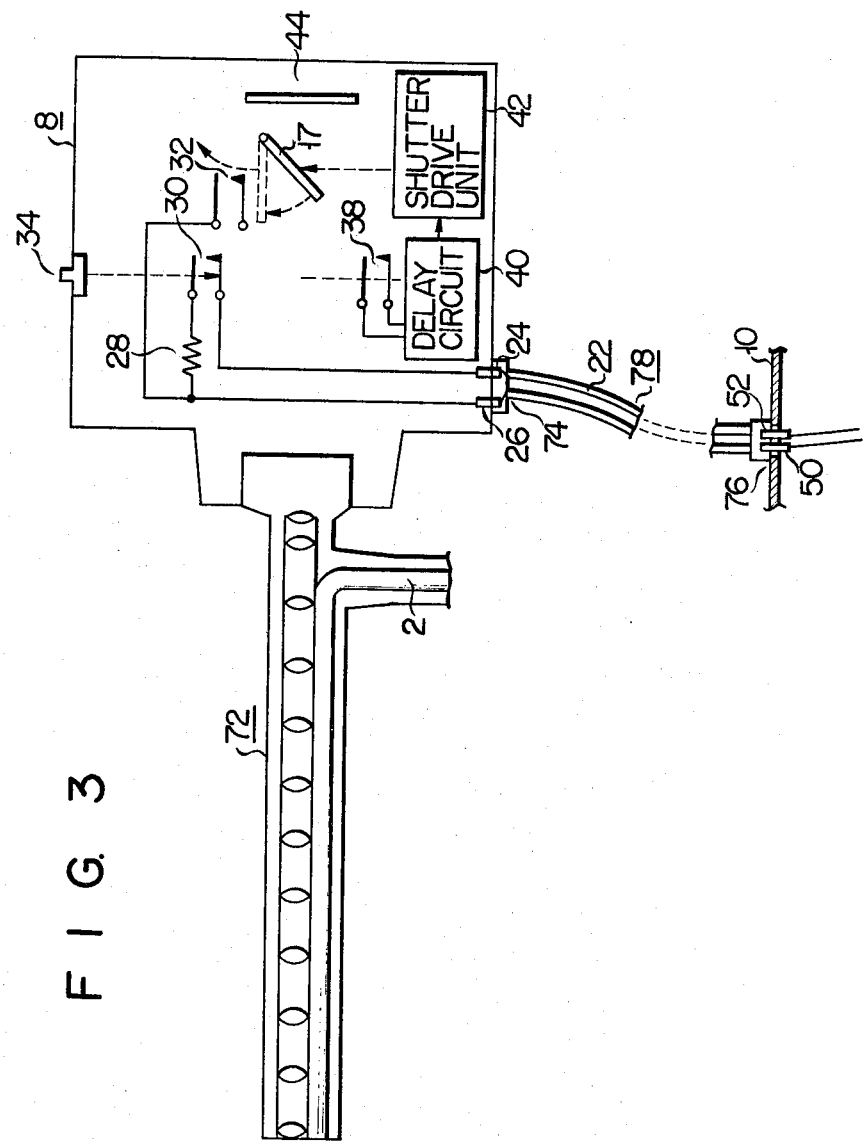
F I G. 3

PHOTOGRAPHING SYSTEM FOR ENDOSCOPE

BACKGROUND OF THE INVENTION

This invention relates to a photographing system for an endoscope and, more particularly, to a photographing system for an endoscope, in which observation light from an observation light source is used for observing a region of interest and photographing light from a photographing light source is used for photographing the region of interest.

In the usual photographing system for an endoscope, an observation light from an observation light source, for instance a halogen lamp, and a photographing light from a photographing light source, for instance an electric flash tube, can be introduced into a light guide of the endoscope. In an optical path, an optical path switching mirror is provided for directing the observation light to the light guide at the time of the observation and directing the photographing light to the light guide at the time of the photographing.

The problems in such an endoscopic photographing system are that the color reproduction of the photograph image is likely to be deteriorated, or the photograph image is likely to become blurred. The region for this is as follows. Usually, the optical path switching mirror is shifted simultaneously with or after the releasing of the shutter of the camera unit. However, at the time of the shifting of the mirror, a mechanical delay is involved, so that not only the photographing light but also the observation light is supplied after the releasing of the shutter. The dual exposure of the film to both photographing light and observation light blurs the resultant photograph image and also deteriorates the color reproduction thereof.

The object of the invention is to provide a photographing system for an endoscope, which prevents the exposure of a film in the camera unit to the observation light and permits exposure only to the photographing light at the time of the photographing, thus permitting a photograph of high clarity and good color reproduction to be obtained.

SUMMARY OF THE INVENTION

According to the invention, there is provided a photographing system for an endoscope comprising:

an endoscope including a light guide for transmitting light to a region of interest for photographing or observation and an image guide for transmitting an image of said region of interest;

a light source unit including a light source for producing photographing light which is supplied to said light guide through a first optical path, a light source for producing observation light which is supplied to said light guide through a second optical path, an optical path switching means for switching the second optical path to the first optical path, a means for energizing said photographing light source, and a means for operating light path switching means; and a camera unit including a shutter means for opening an optical path from said image guide to a film, a shutter drive means for driving said shutter, a shutter release button for producing an instruction signal for starting a photographing cycle, a means for producing an optical path switching signal for energizing said operation means in synchronism to the instruction signal, a means for producing a shutter release signal for starting said shutter drive means predetermined time period after the receiving the instruction signal, and a means for producing a photographing light emission signal for starting said energizing means in synchronism to the release of said shutter means.

BRIEF DESCRIPTION OF THE DRAWINGS

FIG. 3 is a schematic representation of a different embodiment of the photographing system for an endoscope according to the invention.

DETAILED DESCRIPTION

Figure 1:
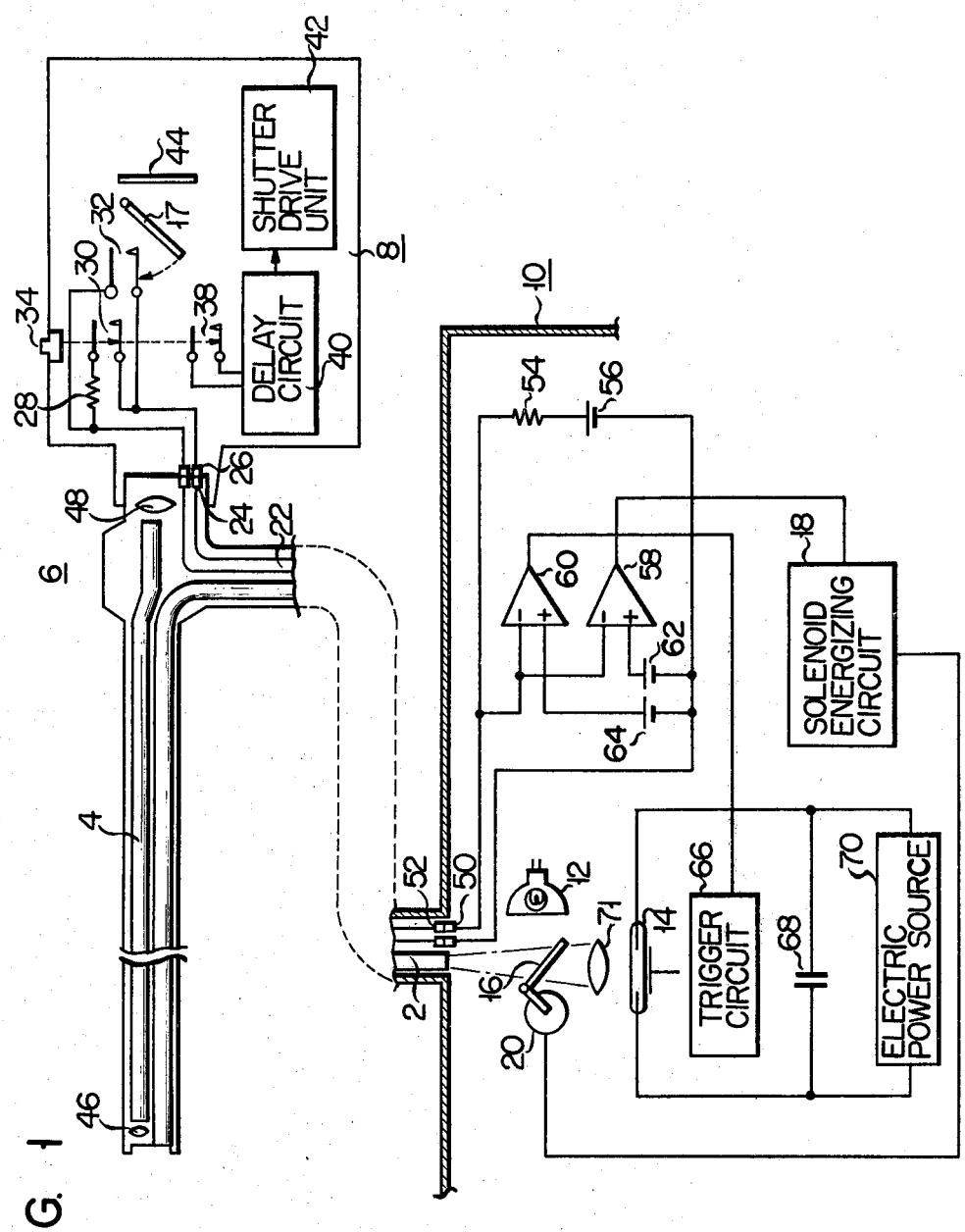
FIG. 1 is a schematic representation of an embodiment of the photographing system for an endoscope according to the invention.

Referring now to FIG. 1, there is shown an embodiment of the endoscopic system according to the invention. A photographing system for an endoscope comprises an endoscope 6, which includes a light guide 2 and an image guide 4, a camera unit 8 coupled to the endoscope 6, and a light source unit 10 for supplying light to the light guide 2. The light source unit 10 includes an observation light source, for instance a halogen lamp 12, for illuminating the region of interest at the time of making a diagnosis, and a photographing light source, for instance an electronic flash tube 14, for illuminating the region of interest at the time of photographing that region. A reflective mirror 16 is so arranged to reflect the observation light to the end face of the light guide 2 and to prevent the photographing light from being transmitted to the end face of the light guide 2. The mirror 16 is mounted on a solenoid 20 driven by a solenoid energizing circuit 18 such that it can be shifted by the solenoid to direct the photographing light to the end face of the light guide 2. The endoscope 6 is provided with a synchronizing cord 22 which electrically connects the camera unit 8 and light source unit 10. The synchronizing cord 22 is provided at its one end with connector pins 24, which are connected to connector pins 26 provided on the camera side when the endoscope 6 is mounted on the camera. One of the connector pins 26 on the side of the camera unit 8 are connected through a resistor 28 to a first switch 30 and is also connected to a second switch 32, the resistor 28 and switches 30 and 32 being provided within the camera unit. The second switch 32 practically has a function of a synchronizing switch for turning on the electronic flash tube 14 to be described hereinafter. While the first switch 30 is closed when a camera shutter release button 34 is depressed, the second switch 32 is adapted to be closed with a jerk-up motion of a mirror shutter 17 which is also provided within the camera unit. The camera unit further includes a third switch 38 which is also closed by the shutter release button 34 simultaneously with the first switch 30. The third switch 38 is connected through a delay circuit 40 to a shutter drive circuit 42, which drives the mirror shutter 17. The camera unit 8 further includes a film 44 disposed behind the mirror shutter 17, and the endoscope 6 is provided with a photographing lens 48 which faces the film 44 for projecting the image of the region of interest transmitted through an objective lens 46 and an image guide 4 on the film 44.

The synchronizing cord 22 is provided at the other end with connector pins 52, which are connected to light source side connector pins 50 when the endoscope is coupled to the light source unit 10. One of the light source side connector pins 50 is connected through a resistor 54 to a positive terminal of a DC power source 56 within the light source unit 10. One of the connector pins 50 is connected to the negative input terminal of each of first and second comparators 58 and 60, which have their respective positive input terminals connected through respective DC power sources 62 and 64 to the other connector pin 50, to which the negative terminal of the DC power source 56 is connected. The voltages $V_{s1}$ and $V_{s2}$ of the respective power sources 62 and 64 are set as follows:

$$V_{s1} \geq V_1 \cdot R_1/(R_2 + R_2)$$

and $$0 > V_{s2} > V_1 \cdot R_1/(R_1 + R_2)$$

where $V_1$ is the voltage of the power source 56, $R_1$ is the resistance of the resistor 28 in the camera unit 8, and $R_2$ is the resistance of the resistor 54 in the light source unit 10.

The circuit elements 54, 56, 58, 60, 62 and 64 constitute a circuit for detecting the on-off states of the first and second switches 30 and 32. The output terminal of the first comparator 58 is connected to the solenoid energizing circuit 18 for operating the solenoid 20, which is thus energized according to the output of the comparator 58. The output terminal of the second comparator 60 is connected to a trigger circuit 66 for triggering the electronic flash tube 14, which is thus energized according to the output of the second comparator 60. The discharging circuit for the flash tube 14 has a well-known construction having a main capacitor 68 and an electric power source 70 as shown in FIG. 1.

Between the flash tube 14 and the end face of the light guide 2 a condenser lens 71 for focusing photographing light from the flash tube 14 onto the end face is provided.

With the above construction of the photographing system for an endoscope according to the invention, at the time of the diagnosis the region of interest (not shown) is observed by observation light from the observation light source 12. At this time, the observation light is reflected by the mirror 16 and introduced into the light guide 2. The observation light transmitted through the light guide 2 is reflected from the region of interest and is led through an objective lens 46 to the image guide 6, so that the image of the region of interest can be observed through the photographing lens 48, mirror 17 and a prism (not shown).

Figure 2A:
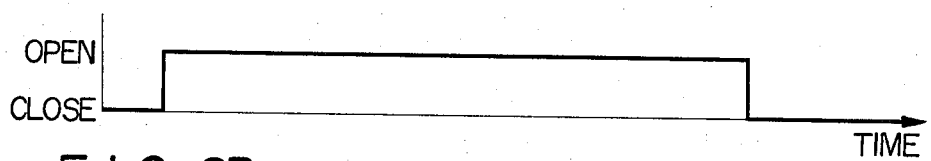
FIGS. 2A to 2M are waveforms illustrating the operation of various parts of the embodiment of FIG. 1, with FIG. 2A showing the operation of a shutter release button, FIG. 2B showing the "on" and "off" states of first switch, FIG. 2C showing the "on" and "off" states of a third switch, FIG. 2D showing the operation of a mirror shutter drive circuit, FIG. 2E showing the open and closed states of a mirror shutter, FIG. 2F showing the "on" and "off" states of a second switch, FIG. 2G showing the output voltage of a first comparator, FIG. 2H showing the operation of a solenoid drive circuit, FIG. 2I showing the operation of a mirror, FIG. 2J showing the operation of a trigger circuit, FIG. 2K showing the amount of photographing light from an electric flash, FIG. 2L showing the amount of light introduced into a light guide, and FIG. 2M showing the amount of light reaching a film within a camera unit.
Figure 2B:
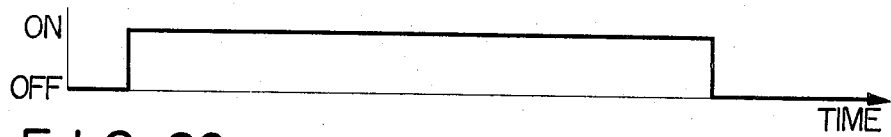
Figure 2C:
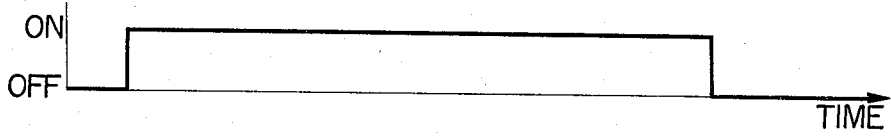
Figure 2D:
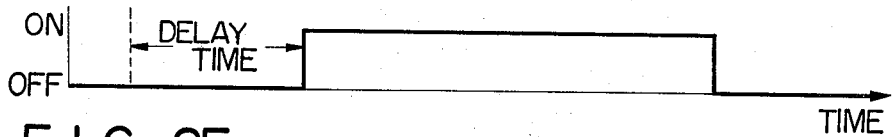
Figure 2E:
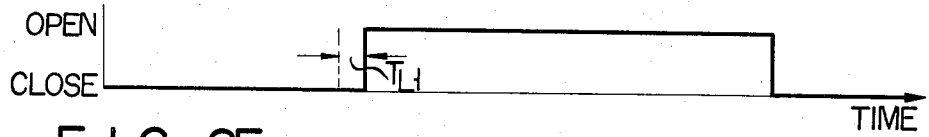
Figure 2F:
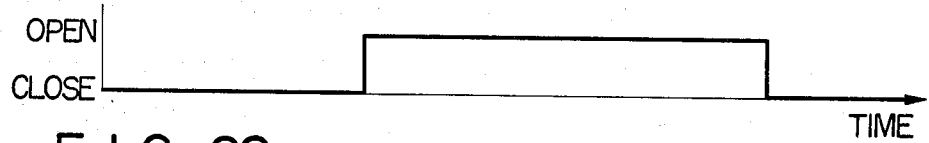

For photographing the region of interest, the shutter release button 34 is depressed as shown in FIG. 2A, whereupon the first and third switches 30 and 38 are simultaneously closed as shown in FIGS. 2B and 2C. With the closure of the third switch 38 the delay circuit 40 is energized. When a predetermined delay time set in the delay circuit 40 is elapsed, the shutter drive circuit 42 is rendered operative as shown in FIG. 2D, whereupon the mirror shutter 17 starts to move. The mirror shutter 17 is completely removed from the optical path between the photographing lens 48 and film 44 not as soon as the shutter drive circuit 42 is rendered operative, but after the lapse of a short mechanical delay time $T_{L1}$, as shown in FIG. 2E. When the mirror shutter 17 is completely removed from the optical path, the second switch 32 is closed as shown in FIG. 2F, and the exposure of the film 44 is enabled.

Figure 2G:
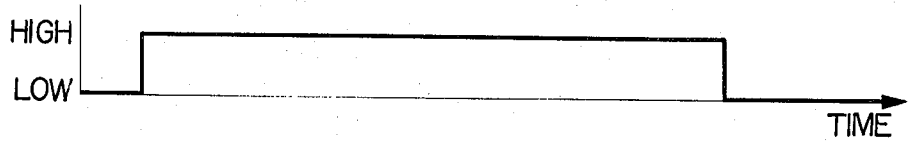
Figure 2H:
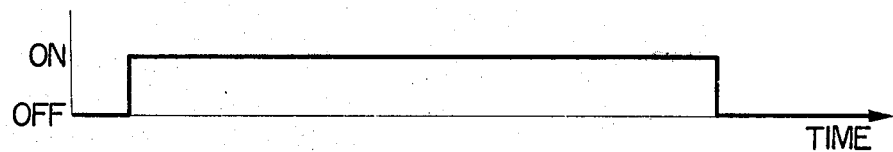
Figure 2I:
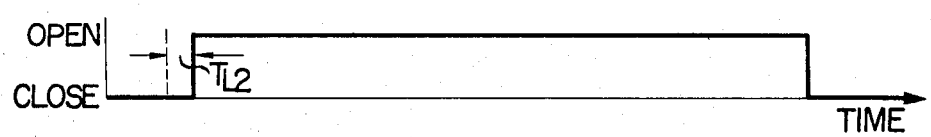

With the closure of the first switch 30 the voltage on the negative input terminals of the comparators 58 and 60 is reduced from the level of the voltage $V_1$ of the power source 56 to $V_1 \cdot R_1/(R_1 + R_2)$. As a result, only the first comparator 58 is rendered operative as shown in FIG. 2G, thus rendering the solenoid energizing circuit 18 operative as shown in FIG. 2H to energize the solenoid 20. Thus, the mirror 16 is completely removed from the optical path between the electronic flash tube 14 and light guide 2 after a mechanical delay time $T_{L2}$ as shown in FIG. 2I. Consequently, light from the observation light source 12 is no longer introduced into the light guide 2, and light from the sole photographing light source 14 can be introduced into the light guide 2.

Figure 2J:
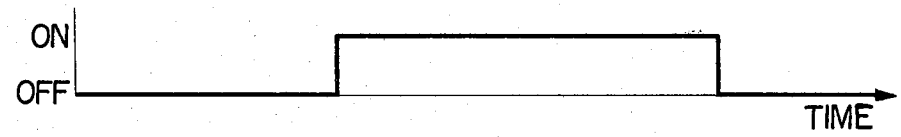
Figure 2K:
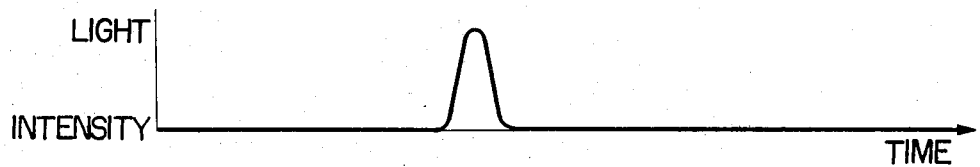

When the second switch 32 is closed after the mechanical delay time $T_{L1}$ from the instant of start of the releasing of the mirror shutter as shown in FIG. 2E after the lapse of the delay time as shown in FIG. 2D, the voltage on the negative input terminals of the comparators 58 and 60 is reduced from the value $V_1 \cdot R_1/(R_1 + R_2)$ substantially to the level of the negative side potential on the power source, whereupon the comparator 60 is rendered operative to produce an output supplied to the trigger circuit 66. As a result, the trigger circuit 66 is rendered operative as shown in FIG. 2J, causing the electronic flash tube 14 to emit light as shown in FIG. 2K. This light is introduced as photographing light to the light guide 2 for illuminating the region of interest, and reflected light therefrom is led through the objective lens 46, image guide 4 and photographing lens 48 to the film surface 44.

Figure 2L:
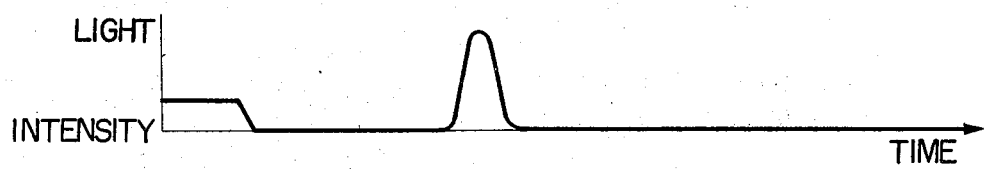
Figure 2M:
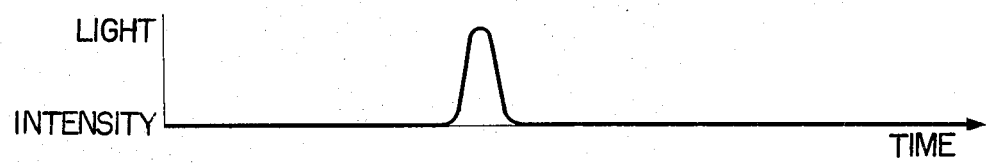

While the observation light is introduced into the light guide 2 as shown in FIG. 2L until the completion of switching of the mirror 16 as shown in FIG. 2I, the mirror shutter 17 is released as shown in FIG. 2E after the switching the mirror 16. Thus, the image of the region of interest obtained by the sole photographing light is transmitted to the film surface 44 as shown in FIG. 2M. It is thus possible to solve the prior-art problem of the dual exposure of the film to the observation light and photographing light.

FIG. 3 shows a different embodiment of the photographing system for an endoscope using a rigid endoscope 72. In this embodiment, synchronizing cord 22 is not provided within the endoscope, but it is provided within a cord 78 having exclusive connectors 74 and 76. The reason for using such an exclusive cord 78 is that it is difficult to provide the cord 22 within the rigid endoscope 72 from the standpoint of sterilization. In the embodiment of FIG. 3 the corresponding parts to those shown in FIG. 1 are designated by like reference numerals, and their description is omitted here. As is described in the embodiment of FIG. 3, various modifications of the wiring of the photographing system are possible. Further, it is possible to appropriately modify the circuit construction of the photographing system according to the invention.

As has been described in the foregoing, according to the invention it is possible to provide a photographing system for an endoscope, which not only eliminates blur due to dual exposure but also permits to obtain photographic images of good color reproduction since the mirror shutter is released for photographing the region of interest after the switching of the observation light source to the photographing light source.

What is claimed is:

1. A photographing system for an endoscope comprising:
    an endoscope including a light guide for transmitting light to a region of interest for photographing or observation, and an image guide for transmitting an image of said region of interest;
    a light source unit including a first light source for producing photographing light which is supplied to said light guide through a first optical path, a second light source for producing observation light which is supplied to said light guide through a second optical path, an optical path switching means for selectively switching the second optical path to the first optical path, energizing means for energizing said first photographing light source, and operating means for operating said optical path switching means; and
    a camera unit having film therein, and including a shutter means for opening an optical path from said image guide to said film, a shutter drive means for driving said shutter means, a shutter release button for producing an instruction signal for starting a photographing cycle, means coupled to receive said instruction signal for producing an optical path switching signal for energizing said operating means of said light source unit in synchronism with said instruction signal, delay means coupled to receive said instruction signal for producing a shutter release signal for starting said shutter drive means a predetermined delay time period after receiving said instruction signal, said delay time period being at least as long as the time required to switch said second optical path to said first optical path, said shutter drive means being coupled to said delay means to receive said shutter release signal from said delay means and for driving said shutter means responsive to said shutter release signal, and means coupled to said shutter means and to said energizing means of said light source unit for producing a photographing light emission signal for starting said energizing means in synchronism with the release of said shutter means to cause said first light source to produce light, whereby observation light is prevented from reaching the film in said camera unit.

2. A photographing system for an endoscope according to claim 1, which further comprises electrical conductor means for transmitting signals from said camera unit to said light source unit.

3. A photographing system for an endoscope according to claim 2, wherein said electrical conductor means is provided within said endoscope.

4. A photographing system for an endoscope according to claim 1, wherein said light source unit further includes means for discriminating input signals supplied from said camera unit and for selectively producing start signals for operating said operating means and for starting said energizing means in correspondence with said input signals from said camera unit.

5. A photographing system for an endoscope according to any one of claims 1, 2, 3 or 4, wherein said shutter means in said camera unit is a mirror shutter.

* * * * *

UNITED STATES PATENT AND TRADEMARK OFFICE
CERTIFICATE OF CORRECTION

PATENT NO. : 4,367,024

DATED : January 4, 1983

INVENTOR(S) : Syuichi TAKAYAMA

It is certified that error appears in the above-identified patent and that said Letters Patent is hereby corrected as shown below:

COLUMN 1, line 25, change "region" to --reason--;

COLUMN 4, line 61, change "synchronizing cord 22" to

--a synchronizing cord 22--.

Signed and Sealed this

Third Day of May 1983

[SEAL]

Attest:

GERALD J. MOSSINGHOFF

Attesting Officer    Commissioner of Patents and Trademarks